United States Patent
Kiedrowski

(10) Patent No.: US 11,659,984 B2
(45) Date of Patent: May 30, 2023

(54) ENDOSCOPE WITH BONDED LIGHT GUIDE

(71) Applicant: Olympus Winter & Ibe GmbH, Hamburg (DE)

(72) Inventor: Gregor Kiedrowski, Hamburg (DE)

(73) Assignee: OLYMPUS WINTER & IBE GMBH, Hamburg (DE)

( * ) Notice: Subject to any disclaimer, the term of this patent is extended or adjusted under 35 U.S.C. 154(b) by 86 days.

(21) Appl. No.: 16/884,478

(22) Filed: May 27, 2020

(65) Prior Publication Data

US 2020/0375442 A1 Dec. 3, 2020

(30) Foreign Application Priority Data

Jun. 3, 2019 (DE) .......................... 102019114763.8

(51) Int. Cl.
| | | |
|---|---|---|
| *A61B 1/07* | (2006.01) |
| *A61B 1/00* | (2006.01) |
| *A61B 1/307* | (2006.01) |
| *B29C 65/48* | (2006.01) |

(52) U.S. Cl.
CPC .............. *A61B 1/07* (2013.01); *A61B 1/0011* (2013.01); *A61B 1/307* (2013.01); *B29C 65/486* (2013.01)

(58) Field of Classification Search
CPC .............. A61B 1/0011; A61B 1/00165; A61B 1/00167; A61B 1/0017; A61B 1/07; G02B 23/26
USPC .................................................. 600/128, 129
See application file for complete search history.

(56) References Cited

U.S. PATENT DOCUMENTS

| | | | | |
|---|---|---|---|---|
| 4,173,392 A | * | 11/1979 | Ekinaka .................... | A61B 1/07 385/117 |
| 4,838,859 A | * | 6/1989 | Strassmann ........ | A61B 1/00156 604/95.03 |
| 4,986,622 A | * | 1/1991 | Martinez ................ | A61B 1/317 362/263 |
| 5,116,317 A | * | 5/1992 | Carson, Jr. .......... | A61B 1/00082 600/116 |
| 5,193,135 A | | 3/1993 | Miyagi | |
| 5,335,647 A | * | 8/1994 | Brustad .............. | A61B 1/00165 385/117 |

(Continued)

FOREIGN PATENT DOCUMENTS

| | | |
|---|---|---|
| DE | 41 35 988 A1 | 5/1992 |
| DE | 10 2016 111 363 A1 | 12/2017 |

(Continued)

OTHER PUBLICATIONS

Epoxy Technology Inc., Safety Data Sheet Epo-Tek 310M-1 Part A & 310M-1 Part B, Nov. 7, 2014, Epoxy Technology Inc., Revision 1, pp. NPL-1 to NPL-12 (Year: 2014).*

*Primary Examiner* — Aaron B Fairchild
*Assistant Examiner* — Stephen Floyd London
(74) *Attorney, Agent, or Firm* — Scully, Scott, Murphy & Presser, P.C.

(57) ABSTRACT

A medical endoscope including: an elongated shaft with a distal end region having a non-circular cross-section and a shaft main section arranged proximally from the distal end region, an at least one light guide having a plurality of individual fibres disposed longitudinally through the shaft, wherein at least a portion of the plurality of individual fibres in the distal end region are bonded over a length of at least 50% of the distal end region with an inflexible adhesive.

8 Claims, 2 Drawing Sheets

(56) References Cited

U.S. PATENT DOCUMENTS

| | | | | |
|---|---|---|---|---|
| 5,554,100 | A | * | 9/1996 | Leiner ..................... A61B 1/07 |
| | | | | 600/920 |
| 5,617,498 | A | * | 4/1997 | Cawood ............. A61B 1/00181 |
| | | | | 385/117 |
| 2005/0165315 | A1 | * | 7/2005 | Zuluaga ............... A61B 5/0084 |
| | | | | 600/476 |
| 2007/0088200 | A1 | | 4/2007 | Dahmen et al. |
| 2008/0015558 | A1 | * | 1/2008 | Harlan .................. A61M 25/09 |
| | | | | 606/15 |
| 2013/0223802 | A1 | | 8/2013 | Dahmen |
| 2017/0035277 | A1 | * | 2/2017 | Kucharski ................ A61B 1/06 |
| 2018/0125336 | A1 | * | 5/2018 | Goldfarb ............... A61B 1/0014 |
| 2021/0196107 | A1 | * | 7/2021 | Blazejewski .......... A61B 1/018 |

FOREIGN PATENT DOCUMENTS

| | | |
|---|---|---|
| DE | 10 2018 102 385 A1 | 8/2019 |
| EP | 0 058 574 A2 | 8/1982 |
| EP | 1 776 918 A2 | 4/2007 |
| EP | 2 617 348 A1 | 7/2013 |
| JP | S59-222802 A | 12/1984 |
| WO | 2019/149877 A1 | 8/2019 |

* cited by examiner

ENDOSCOPE WITH BONDED LIGHT GUIDE

CROSS-REFERENCE TO RELATED APPLICATION

The present application is based upon and claims the benefit of priority from DE 10 2019 114 763.8 filed on Jun. 3, 2019, the entire contents of each of which are incorporated herein by reference.

BACKGROUND

Field

The present disclosure relates generally to a medical endoscope of the type, and a method for its assembly and more particularly to medical endoscopes with an elongated, semi-flexible shaft part.

Prior Art

Medical endoscopes have an elongated, semi-flexible shaft part and are, for example, used in urology and referred to there as urethroscopes or ureteroscopes. Urethroscopes are used for endoscopic work in the ureter and in the renal pelvis to observe the surgical site and to introduce insertable instruments. In order to reach the operation area endoscopically, i.e. bloodlessly, the urethroscope is pushed from the outside through the urethra into the bladder, from there through the ostium (mouth of the ureter with a flap) into the ureter and advanced into the surgical area, e.g. up to a stone or a narrowing in the ureter or to the renal pelvis. In order to reach these regions, the shaft tube of the urethroscope generally has a length of at least about 330 mm.

Optics for observing the operation area, at least one optical fibre bundle for illumination and one or a plurality of working channels through which insertable instruments such as catheters, forceps, stone traps, lithotripters (stone shattering devices), etc., can be guided to the surgical site generally run within the shaft tube. Since the ureter and especially the ostium is very narrow, the maximum tolerable shaft diameter is very limited. Generally, the diameter should not be larger than about 3 to 4 mm. This results in a very long and thin configuration of the shaft tube. The optics can advantageously be designed as an image guide fibre bundle. This enables shaft tubes with a sufficiently high degree of flexibility (semi-flexibility), which contributes to the fact that interventions can be carried out particularly gently.

The main parts of the shaft tube generally have a round cross-section. In order to reduce the diameter in the distal end region to a minimum, in some endoscopes, such as OES Pro single channel ureteroscopes (Olympus) and OES 4000 dual channel ureteroscopes (Olympus), this region is provided with a non-circular cross-section. Depending on the number of working channels, the end region in these instruments is then either oval (one channel) or substantially triangular (two channels). The circumference of the distal end region can thereby be reduced, so that this endoscope section can be guided to the surgical site even more gently. Such ureteroscopes are described, for example, in DE 10 2016 111 363 A1.

The optical fibre bundles can be drawn in freely in the interior of an endoscope or can be protected, for example, by a shrinkage tubing surrounding the bundle, i.e. a tube that wraps around the fibre bundle under exposure to heat. If the shaft part is deformed elastically, exposed optical fibres run the risk of being damaged by other components of the shaft part, since these components exert pressure or friction on the fibre optic bundle and can thus damage individual fibres. As a result, the light output at the distal end of the fibre bundle can be significantly reduced. A surrounding shrinkage tubing protects against this damage. In the aforementioned DE 10 2016 111 363 A1, flexible bonding of the optical fibres in the round shaft section is alternatively proposed. These protective devices for optical fibres have so far only been used in the round cross-section of the urethroscope, since this is where the greatest deformation of the shaft occurs during an operation and where the risk of damage is the greatest.

It has now been found that damage to the optical fibres is not only caused in the round, stronger bend part of the shaft, but also in the distal end region, which is generally subjected to relatively few bends. In this region, due to the significantly reduced diameter, protection of optical fibre bundles by, for example, a shrinkage tubing, is not possible.

SUMMARY

An object is this to provide endoscopes whose optical fibre bundles are not damaged during use and in which at the same time the volume occupied by the optical fibre in the interior of the shaft part is kept as low as possible.

Such object can be solved by an endoscope in which the optical fibres of a light guide in the distal end region of the endoscope shaft are bonded using an inflexible adhesive. This stabilises the light guide in the distal end region and protects it from damage caused by deformation, friction or pressure. It is not necessary to protect the light guide in this shaft section by covering it with a separate light guide channel, a shrinkage tubing or by bonding it with a flexible adhesive. Surprisingly, it has been found that the optical fibres also require mechanical protection in this region. Furthermore, it has surprisingly been found that the protective effect can be achieved with an inflexible adhesive. Therefore, only a single type of adhesive has to be used in the distal end region, so that there are no interactions between different types of adhesive.

In a first aspect, a medical endoscope can be provided with an elongated shaft part with a distal end region with a non-circular cross-section and a shaft main section arranged proximally therefrom, wherein the shaft part is passed through in the longitudinal direction by at least one light guide having a plurality of individual fibres, wherein fibres of the light guide in the distal end region are bonded over a length of at least 50% of the distal end region by means of an inflexible adhesive, such as, over the entire length of the distal end region.

The medical endoscopes can have an elongated shaft part with a distal end region with a non-circular cross-section and a shaft main section arranged proximally therefrom, and a control part for the operator adjoining it proximally. The shaft part can be formed by a sealed housing. This can be configured, for example, in the form of a stem tube. In other words, the shaft part can comprise an outer stem tube or outer tube. In addition, the shaft part can contain inner tubes that run inside the outer tube, as well as various elements drawn into the shaft part, such as, for example, working channels, fibre tubes, optical channels, other light guides, and the like.

Suitable materials such as steel, from which the housing of the shaft part can be made, are known to the person skilled in the art. Materials that ensure sufficient flexibility of the shaft part can be used. The shaft part can bend during examinations in order to follow the organ passages, such as the urethra and the ureters.

The medical endoscope can be a urethroscope. Urethroscopes (also synonymous with ureteroscopes) are used for examinations of the ureters and therefore can have a long shaft part that must have a corresponding flexibility. Alternatively, the medical endoscope can also be any other endoscope that has or can have a semi-flexible shaft part. In this context, "semi-flexible" means that the shaft part is only elastically deformable in use, i.e. it can be bent and return to its original shape when the bending force increases.

The length of the shaft part can be so long that convenient handling and accessibility to the operating site is guaranteed. Thus, the shaft part can have a length of approximately 200 mm to 600 mm, such as 300 mm to 500 mm, or approximately 330 mm to 430 mm. The diameter of the shaft part can be very small. The shaft part can have a diameter of approximately 0.5 mm to 8 mm, such as approximately 1 mm to 5 mm, or 2 mm to 4 mm. The ratio of the shaft diameter to the length of the shaft can be selected so that the shaft is flexible or bendable, at least in sections, such as elastically deformable, i.e. reversibly bendable. It has been found that this slight, tolerated bend does not damage the optical fibres protected in the distal end region by an inflexible adhesive.

The distal end region can have a non-circular cross-section, i.e. the cross-section deviates from the circular shape in this region, i.e. is not circular. The section can, for example, be oval or triangular, wherein in the latter alternative the corners of the triangular shape can be rounded. With these cross-sectional shapes, the circumference of the distal end region can be reduced to a minimum, so that the endoscope user is able to move the distal end of the endoscope gently into the desired region.

In contrast to the distal end region, the shaft main section can have a round cross-section. The shaft wall can also be thicker in the shaft main section. The shaft main section can have a larger circumference than the distal end region. It goes without saying that the maximum diameter of the shaft main section in these embodiments can also be larger than the maximum diameter of the distal end region. In this way, greater loads can be taken into account, which can affect the shaft main section.

The "distal end region" extends over the entire distal region, in which the shaft part has a non-circular cross-section. This means that the distal end region can, for example, generally extend proximally beyond the region in which the distal lens system of optics is arranged. The distal end region of the shaft part can, for example, have a length of approximately 70 mm or more, such as approximately 80 mm or more, approximately 90 mm or more, or approximately 100 mm. In other words, the distal end region of the shaft part can have a length of approximately 70 mm to 240 mm, such as approximately 80 mm to 170 mm, or approximately 90 mm to 150 mm.

The shaft part can be passed through in the longitudinal direction by at least one light guide having a plurality of individual fibres (optical fibres). This means that the shaft part can be passed through by one or more light guides, for example, one, two or three light guides, such as two light guides. The following description applies to all light guides if there is a plurality of these in one shaft part.

The light guide, which can have a plurality of individual fibres, extends substantially through the entire length of the shaft part, i.e. through the shaft part from the proximal end of the shaft main section to the distal end of the distal end region. Since the light guide is protected in the distal end region by bonding with an inflexible adhesive, the light guide will remain substantially intact even after regular use of the endoscope. This means, for example, that even after repeated use, more than 70%, such as more than 80%, or more than 90% of the fibres of the light guide in the distal end region of the shaft part are intact. In this context, "intact" means that the light conduction through the fibre is not substantially affected by damage such as tearing of the fibre.

The light guide can be suitable for guiding light from a light source to the distal end of the shaft part. Suitable light guides having a plurality of individual fibres are known to the person skilled in the art and are routinely used in endoscopy or urethroscopy. The light guide can be configured as an optical fibre bundle, i.e. as a bundle of optical fibres. An optical fibre bundle can have in each case a plurality of optical fibres, e.g. a plurality of glass fibres. Optical fibres can be glass fibres or fibres, for example, based on plastic. The light guide or the optical fibre bundle can be coupled or connected to an external light source. The light guide, i.e. the optical fibre bundle, can have a thickness of 0.4 to 0.8 mm, or 0.5 to 0.71 mm.

In this context, the term "bundle" should not be understood to mean that the collection of optical fibres must have a round cross-section. While the light guide, such as the optical fibre bundle, can have a round cross-section, other cross-sectional shapes by means of which the light guide can be better fitted under certain circumstances into the free space within the shaft part, are also possible. For an arrangement that is as space-saving as possible, the cross-sectional shape of an optical fibre bundle can be adapted, for example, to the outer contours of the further components running inside the shaft part.

The fibres of the light guide can be bonded in the distal end region using an inflexible adhesive. The adhesive protects the optical fibres within the distal end region against pressure and friction and thus against destruction during use. By bonding, the light guide runs through the distal end region immediately adjacent to—or only separated by an adhesive layer—other channels, such as the working channel and the optics channel (also known as the optics channel). Additional protection of the light guide in the distal end region by means of a sheathed tubing or tube may not be necessary.

Fibres of the light guide can be bonded in the distal end region on a length of at least 50% of the distal end region by means of an inflexible adhesive, such as about 100%. Accordingly, fibres of the light guide can be bonded on a length (along the longitudinal axis of the light guide or shaft part) of 50% or more, or a length of 65% or more, such as on 80% or more of the length of the distal end region by means of an inflexible adhesive. In other words, fibres of the light guide can be bonded on a length of 50% to 100%, such as a length of 65% to 100%, or a length of 80% to 100% of the distal end region by means of an inflexible adhesive. The optical fibres can be bonded substantially over the entire length of the distal end region. In contrast to this, the optical fibres in conventional endoscopes are only bonded to a lens or the like at their distal end by means of an inflexible adhesive. The usual bonding does not extend over a longer section of the shaft part.

As used herein, "bonded" means that two or more fibres of an optical fibre bundle adhere to one another by means of an adhesive. It may be sufficient to bond the outer fibres of an optical fibre bundle to one another in order to ensure adequate protection. Generally, capillary forces will also cause the adhesive to permeate the optical fibre bundle when the adhesive is applied. As an alternative or in addition, the fibres can be bonded to one another in the interior of a light guide by additionally introducing adhesive between the fibres.

In addition to bonding the optical fibres to one another, one or a plurality of fibres can also be glued to other components of the endoscope. For example, the light guide can be connected to the shaft wall within the distal end region by means of the adhesive, e.g. with the inner wall of an outer tube of the shaft part. As a result, the mechanical protection of the optical fibres can be improved even more, since frictional forces acting on the fibres are reduced. Furthermore, the interior of the shaft—insofar as it is not filled by other insertable instruments and inner tubes—can be sealed off from the outside of the shaft in this way. In one embodiment, the adhesive thus also seals the distal end region in a gas-tight and/or liquid-tight manner. This means that no gases and/or liquids can enter the interior of the shaft through the distal end of the endoscope. It goes without saying that channels running inside the shaft part, such as channels for liquid exchange and channels for insertable instruments, are excluded from this sealing function of the adhesive. The adhesive only seals the free space inside the shaft part.

The adhesive used for bonding can be an inflexible adhesive. This means that the adhesive can only be mechanically deformed to a limited extent after it has hardened, such as, that the adhesive cannot or can only insignificantly be deformed or bendable after it has hardened. Vice versa, "more bendable" means "more easily or absolutely elastically deformable". Any inflexible adhesive can be used to bond the fibres of the light guide in the distal end region. After curing, the adhesive can be rigid enough to fix the light guides to one another and to protect them from significant deformation. The following information can relate to the properties of the adhesive after it has been cured.

The adhesive can be grinded, i.e. it can have a hardness sufficient for it to be grinded and polished. Suitable inflexible, grindable adhesives are, for example, adhesive with a Shore D hardness of 60 or more, such as 70 or more, such as 75 or more. Two-component adhesives can also be used. In these, a chemical curing reaction is started by mixing two adhesive components. Two-component adhesives include, for example, unsaturated polyester resins, epoxy resins, methyl methacrylate adhesives and fibrin adhesives. The inflexible adhesive can be an epoxy adhesive. Suitable epoxy adhesives are commercially available and known to the person skilled in the art. A suitable epoxy adhesive is, for example, EPO-TEK® 354 (Epoxy Technology, Inc.).

A shaft main section can connect proximally to the distal end region. The shaft main section can directly adjoin the distal end region or can be separated from the distal end region by a short transition section. The transition section can be generally no longer than 5 cm, i.e. 5 cm long or less, such as 4 cm or less, or 3 cm or less. The shaft main section can also directly adjoin the distal end region. The shaft main section can lie between the distal end region and the operating part or the main body of the endoscope, which serves to operate and hold the instrument. The operating part of the endoscope can adjoin the shaft main section directly proximally.

The shaft main section can be longer than the distal end region and comprise more than 50% of the length of the shaft part. The shaft main section may, for example, have a length of about 100 mm to 500 mm, such as 200 mm to 380 mm, or 240 mm to 350 mm. In other words, the shaft main section may have, for example, a length of 100 mm or more, such as a length of 200 mm or more, or a length of 300 mm or more. The shaft part can have a distal end region with a length of approximately 80 to 150 mm and a shaft main section arranged proximally therefrom with a length of approximately 240 mm to 380 mm.

The shaft main section can be subjected to a greater bending moment when the instrument is used and usually bends more than the distal end region. In other words, the shaft main section can be is elastically deformable. This enables the user to reach the examination site through the organ passages during handling without damaging the organs. The bending in the shaft part that arises during handling can be, i.e. with proper, normal use of the endoscope, passively reversible, so that the deformation when the load is removed, e.g. when removing the endoscope from the patient's body, disappears, so that the shaft part returns to its normal shape. The shaft main section can have a substantially round cross-section over at least 70% of its length, such as at least 80% of its length.

Since the diameter and the circumference of the shaft part in the shaft main section can be larger than the diameter and the circumference in the distal end region, the optical fibres can be protected here by various means. For example, the light guide in the shaft main section can be sheathed or also bonded, such as being bonding with a flexible adhesive, such as a silicone adhesive. Alternatively, the protection of the light guide in the shaft main section can be by means of a tubing surrounding the light guide. The light guide therefore can run through a tubing, such as a shrinkage tubing, in the shaft main section. This tubing can be a silicone tubing, for example. The use of a tubing ensures that when a flexible section of the shaft part is bent, the light guide can adapt to the movement of the shaft part and at the same time is protected from pressure and friction by other components (e.g. channels) contained in the shaft part. Compared to bonding with a flexible adhesive, the use of a tubing has the advantage that different, potentially interacting adhesives do not have to be used in the assembly of the instrument.

In a further aspect, a method is provided for assembling a medical endoscope, such as an endoscope described herein, wherein the method comprises (a) placing an inflexible adhesive within a distal end region of a shaft part of the endoscope in at least one position, (b) introducing a light guide having a plurality of individual fibres into the shaft part, and (c) curing the adhesive.

In (a), the adhesive that has not yet cured—for example, a two-component adhesive—is placed in at least one position within the distal end region immediately after the two adhesive components have been mixed. With the help of a cannula, for example, a portion of the adhesive can be placed on the inner wall of the outer tube of a shaft part. Further portions of the adhesive can then be placed at one or more further positions of the outer tube, which can be spaced apart from one another in the longitudinal direction.

Immediately following the placement of the adhesive, before the adhesive has cured, the light guide is introduced into the shaft part, such as into the distal end region of the shaft part equipped with adhesive portions. Further components, such as fibre and working channels, can also be introduced at the same time or in a timely manner in order to ensure a tight bond. The light guide can, for example, be drawn into or inserted into the shaft part, wherein drawing into the shaft part is performed.

After the adhesive and the light guide and further components have been introduced into the shaft part, the adhesive is cured or allowed to cure. Suitable methods are known to the person skilled in the art which may differ depending on the type of inflexible adhesive used.

BRIEF DESCRIPTION OF THE DRAWINGS

Exemplary embodiments are shown schematically in the drawings, where.

DETAILED DESCRIPTION

Figure 1:
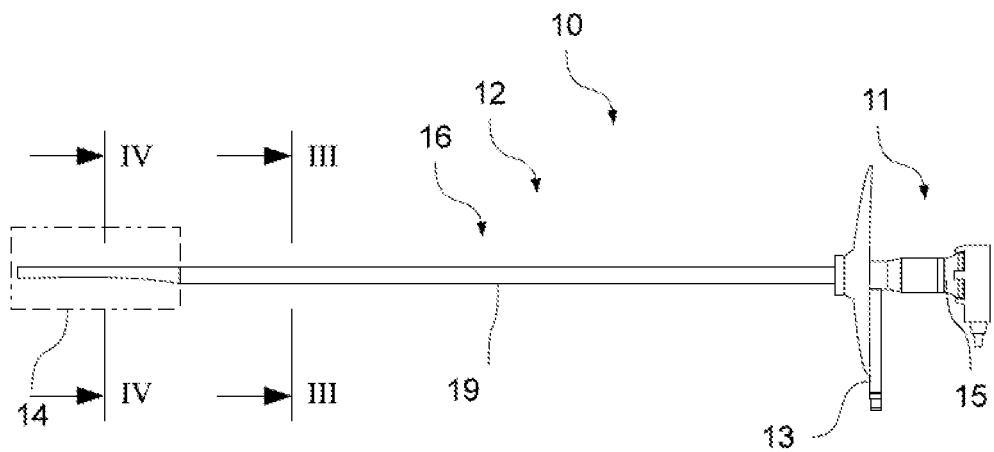
FIG. 1 illustrates a schematic side view of a urethroscope.

FIG. 1 shows a side view of an endoscope 10 with a main body 11 and an elongated tubular shaft part 12 adjoining it distally, which is to be inserted into the patient's body. The main body 11 can, for example, comprise an eyepiece and an introductory part. The shaft part 12 and the main body 11 are connected to one another in a sealed manner in an unspecified manner, for example bonded, soldered or the like.

Figure 2:
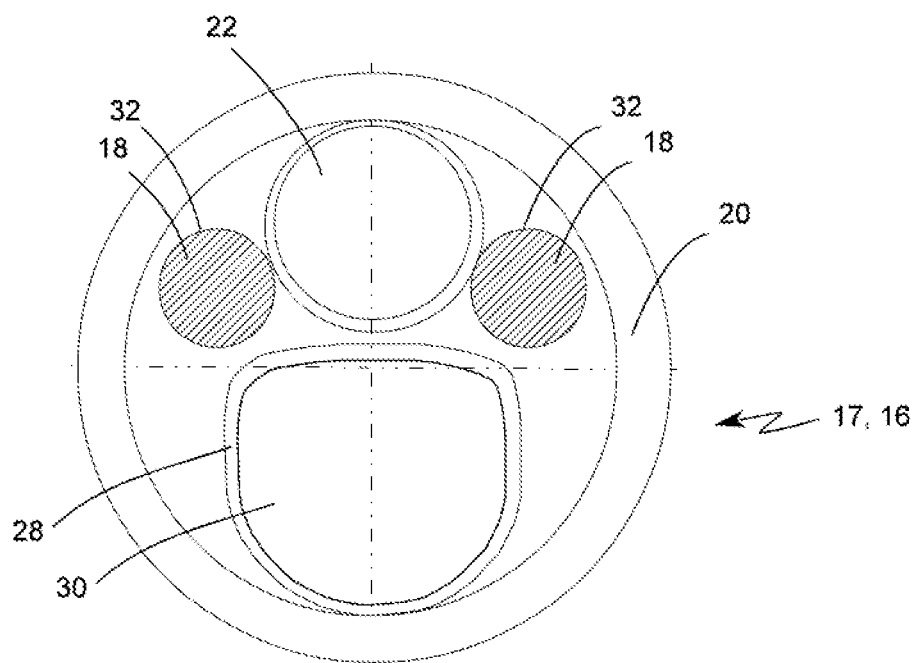
FIG. 2 illustrates a section along line in FIG. 1 through the shaft main section of the shaft part.

In a connecting piece 13 on the main body 11, which is used to connect an external light guide, not shown, the proximal end of a light guide 18 shown in FIGS. 2 and 3 can be attached in the form of an optical fibre bundle which passes through the interior of the shaft part 12 in the longitudinal direction up to the distal end of the shaft part 12.

In addition, an eyepiece socket 15 can extend from the main body 11, through which an optical system runs, which is also guided through the shaft part 12 to the distal end of the endoscope 10. At the proximal end of the optical system, an eyepiece can be provided on the eyepiece socket 15.

The length of the shaft part 12 in an endoscope 10 of conventional design which, like the one shown, is configured as a urethroscope, is 400 to 500 mm, for example. The outer diameter of the shaft part 12, such as the outer diameter of the outer tube 19 of the shaft part 12, typically does not exceed a maximum of approximately 4 mm. In the case of such a diameter of the outer tube 19, it results that, substantially regardless of the wall thickness, there is a certain stiffness of the tube, which, when the tube is bent, leads to an elongation of the material on the outside and a compression of the material on the inside (based on the centre point of the bending radius).

In the shaft part 12 of the endoscope 10 shown in FIG. 1, the distal end region 14 is formed with a smaller outer diameter and circumference than the shaft main section 16 arranged proximally therefrom. As a result, the distal end region 14 can be guided to the surgical site in a particularly gentle manner. The distal end region 14 has a length of approximately 10 cm.

At its distal end, the shaft part 12 or the distal end region 14 is sealed in a suitable manner, for example, with a window for optics in the optics channel 22 shown in FIGS. 2 and 3 and with a sufficiently tight bonding of the light guide(s) 18 shown in FIGS. 2 and 3. The bonding at the distal end is usually performed, for example, using an inflexible adhesive. The well-sealed shaft part 12 ensures that the optics arranged in the interior and the light guide(s) 18 are not impaired by water or steam penetrating when working with the endoscope 10 or during sterilization. Furthermore, the inflexible bonding in the distal end region 14 is continued over the entire length of the distal end region 14. This serves on the one hand to protect the light guide(s) 18 shown in FIGS. 2 and 3 and on the other hand to provide even better gas- and liquid-tight sealing of the shaft part 12.

The cross-sectional illustration 17 of FIG. 2 shows that the shaft part 12 in a shaft main section 16 has a shaft wall 20 which has a round cross-section and which can be configured as a metal tube. The shaft main section 16 and the distal end region 14 are elastically deformable, i.e. reversibly flexible, and can therefore deform flexibly during the surgical procedure.

The interior of the shaft part 12 enclosed by this shaft wall 20 accommodates two inner channels in the exemplary embodiment shown, the optics channel 22 and the working channel 30. Both the optics channel 22 and the working channel 30 can be configured as metal tubes, for example with corresponding walls 28 made of metal, for example, steel. The optics channel 22 encloses the optics, which transmits the viewed image from a lens arranged at the distal end of the shaft part 12 to the eyepiece. The working channel 30 is configured as a free channel in which an instrument (for example, a laser lithotriptor) can be advanced through a connection piece (not shown, the proximally provided laser generator of which is also not shown).

In the interior of the shaft part 12, two light guides 18 are also laid, which can be configured as optical fibre bundles, and serve to illuminate the field of view. The light guides 18 are sheathed in the embodiment shown with a flexible shrinkage tubing 32 made of silicone, which protects the light guides 18 from damage caused by pressure and friction. Alternatively, it is also possible to protect the light guides 18 in each case by bonding with a flexible adhesive, such as a silicone adhesive. With such an adhesive, however, the possible interactions between different types of adhesive must be taken into account when assembling instruments.

At the proximal end of the shaft part 12, the light guide 18 can be led out of the main body 11 via a light guide connection. There, an optical fibre connection cable can be connected to a cold light source, not shown.

Figure 3A:
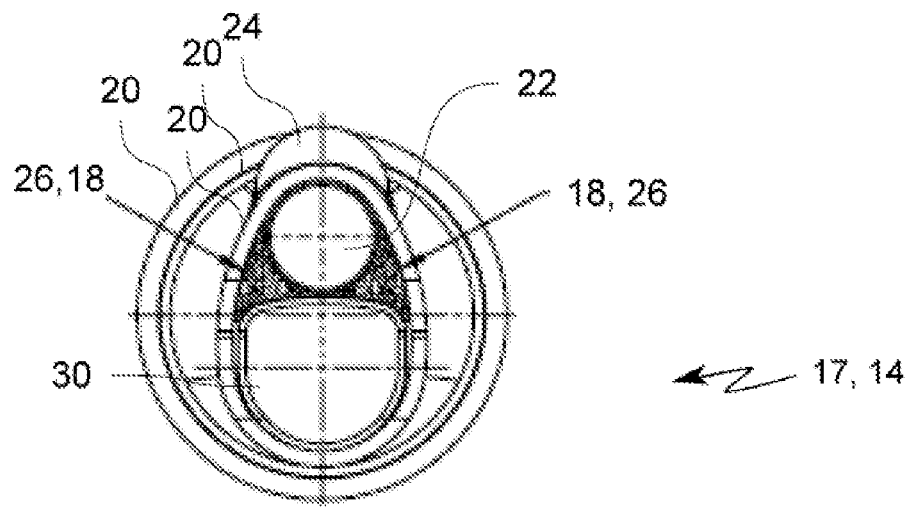
FIG. 3a illustrates a section along line IV-IV in FIG. 1 through a distal end region of the shaft part, wherein the shaft part has a working channel and an optics channel and the end region has a non-circular, oval cross-section.
Figure 3B:
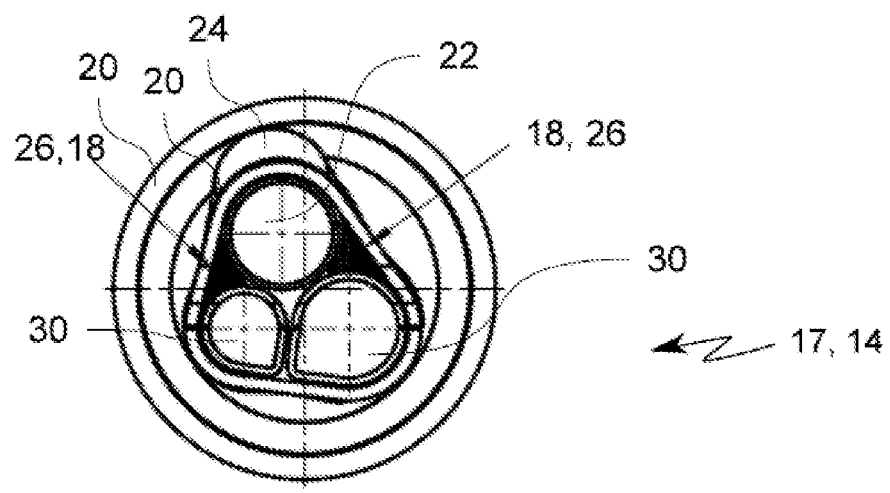
FIG. 3b illustrates a section along a line IV-IV in FIG. 1 through a distal end region of an alternative shaft part, wherein the shaft part has two working channels and an optics channel and the end region has a non-circular, substantially triangular cross-section.

FIG. 3a and FIG. 3b each show a cross-section 17 through a distal, non-circular end region 14 of different shaft parts 12.

It can be seen that the shaft part 12 shown in FIG. 3a has a substantially oval outer cross-section in a distal end region 14, while—as can be seen in the background of FIG. 3a—proximally from this end region 14 it has a shaft main section 16 with a round outer cross-section. The shaft part 12 shown in FIG. 3a is part of a 1-channel instrument, since the shaft part 12 clearly has a single working channel 30.

It can also be seen that the shaft part 12 shown in FIG. 3b has a substantially triangular outer cross-section with rounded corners in its distal end region 14, while—as can be seen in the background of FIG. 3b—proximally from this end region 14 it has a shaft main section 16 with a round outer cross-section. The shaft part 12 shown in FIG. 3b is part of a 2-channel instrument, since the shaft part clearly has two working channels 30.

Due to the oval or triangular outer cross-section of the distal end region 14, the distal end region 14 of the shaft part 12 shown in each case has a circumference which is significantly reduced compared to the shaft main section 16.

In addition to the working channel(s) 30, the shaft parts 12 have an optics channel 22, into which optics can be drawn. A dilation nose 24 is also arranged on the shaft part 12. It can be seen that the light guides 18 substantially fill the entire free space within the shaft part 12. The light guides 18 are bonded with an inflexible epoxy adhesive for protection against breaking and protection against friction. For bonding, portions of the adhesive can be placed on the inside of the shaft wall 20 at a plurality of positions of the respective end region 14 and then the optics channel 22, working channel(s) 30 and the light guides 18 were introduced into the outer tube 19. The epoxy adhesive was then allowed to cure. The adhesive can be applied over the entire length of the distal end region 14 or a portion thereof.

While there has been shown and described what is considered to be preferred embodiments of the invention, it will, of course, be understood that various modifications and changes in form or detail could readily be made without departing from the spirit of the invention. It is therefore intended that the invention be not limited to the exact forms described and illustrated, but should be constructed to cover all modifications that may fall within the scope of the appended claims.

LIST OF REFERENCE NUMERALS

10 endoscope
11 main body
12 shaft part
13 connecting piece
14 distal end region
15 eyepiece
16 shaft main section
17 cross-section shaft part
18 light guide
19 outer tube
20 shaft wall
22 optics channel
24 dilation nose
26 inflexible adhesive
28 wall of the working channel
30 working channel
32 shrinkage tubing

The invention claimed is:

1. A medical endoscope comprising:
a main body;
a rigid elongated shaft having a proximal end connected to a distal end of the main body, the elongated shaft having a distal end region with a non-circular cross-section and a shaft main section arranged between the distal end region and the distal end of the main body, and
at least one light guide having a plurality of individual fibres disposed longitudinally through the shaft,
wherein at least a portion of fibres of the plurality of individual fibres in the distal end region are bonded over a length of at least 50% of the distal end region with a single inflexible adhesive having a hardness so as to be grindable,
the shaft main section has a round cross-section,
the shaft main section has a greater circumference than a circumference of the distal end region,
the at least one light guide within the distal end region is connected to a wall of the shaft with the inflexible adhesive;
the inflexible adhesive has a Shore-D hardness of 75 or more;
the inflexible adhesive is a two-component adhesive; and
the inflexible adhesive seals the distal end region in one or more of a gas-tight manner and a liquid-tight manner.

2. The medical endoscope according to claim 1, wherein the distal end region has a length of 70-240 mm.

3. The medical endoscope according to claim 1, wherein the at least the portion of fibres of the at least one light guide in the distal end region are bonded over a length of at least 65% of the distal end region with the inflexible adhesive.

4. The medical endoscope according to claim 1, wherein the at least one light guide in the shaft main section passes through a tubing at least sectionally.

5. The medical endoscope according to claim 1, wherein the inflexible adhesive is an epoxy adhesive.

6. The medical endoscope according to claim 1, wherein the distal end region has a smaller diameter than a diameter of the shaft main section.

7. A method for assembling the medical endoscope according to claim 1, the method comprising:
placing the inflexible adhesive within the distal end region of the shaft of the endoscope in at least one position,
introducing the at least one light guide having the plurality of individual fibres into the shaft part, and
one of curing the adhesive and allowing the adhesive to cure.

8. The medical endoscope according to claim 1, wherein the inflexible adhesive is an epoxy adhesive having a Shore-D hardness of 82.

* * * * *